United States Patent [19]

Bodenrader

[11] 4,264,448

[45] * Apr. 28, 1981

[54] METHOD FOR BACTERIOLOGICAL TREATMENT OF MANURE AND HIGH BOD INDUSTRIAL WASTES

[76] Inventor: Bonnie J. Bodenrader, 11 Castle Heights Rd., Andover, Mass. 01810

[ * ] Notice: The portion of the term of this patent subsequent to Jul. 29, 1997, has been disclaimed.

[21] Appl. No.: 31,905

[22] Filed: Apr. 20, 1979

Related U.S. Application Data

[63] Continuation-in-part of Ser. No. 963,675, Nov. 27, 1978, Pat. No. 4,214,985.

[51] Int. Cl.$^3$ ............................................... C02F 3/34
[52] U.S. Cl. .................................... 210/611; 210/764; 71/21; 71/25; 426/43
[58] Field of Search ...................... 210/2, 4, 10, 11, 18, 210/64; 71/12, 13, 21, 25, 26; 195/2, 11, 96; 426/43, 53; 435/253, 262, 276, 853–857

[56] References Cited

U.S. PATENT DOCUMENTS

| | | | |
|---|---|---|---|
| 3,546,812 | 12/1970 | Kobayashi et al. | 71/12 X |
| 3,751,338 | 4/1973 | Farris | 210/11 X |
| 3,801,499 | 4/1974 | Luck | 210/11 |
| 3,900,572 | 8/1975 | Peer | 426/43 |
| 3,961,078 | 6/1976 | Stitt | 210/11 X |
| 4,018,650 | 4/1977 | Busta et al. | 210/11 X |

*Primary Examiner*—Thomas G. Wyse
*Attorney, Agent, or Firm*—Thompson, Birch, Gauthier & Samuels

[57] ABSTRACT

Manure from stockyards is treated in a single step by the addition of both a bacteria (*L. plantarum*) and a fermentable carbohydrate (lactose). The pH of the treated manure falls to below 4.0. The manure without more is acceptable as landfill or with further treatment as cattle feed.

17 Claims, No Drawings

METHOD FOR BACTERIOLOGICAL TREATMENT OF MANURE AND HIGH BOD INDUSTRIAL WASTES

This application is a continuation-in-part of application Ser. No. 963,675, filed Nov. 27, 1978, now U.S. Pat. No. 4,214,985.

BACKGROUND OF THE INVENTION

It is conventional practice in the raising of cattle in the United States and in certain other countries, to confine them in so-called feedlots or feedyards where they are fed high-value feed mixes enriched with proteins, carbohydrates, fats, vitamins and minerals to achieve a relatively rapid gain in weight.

The animal industry generally in the United States produces about 2 billion tons of animal manure a year. For example, such feedlots or feedyards may often contain as many as 2,000 to 50,000 head of cattle in a relatively small area. Typically, an average of 18 pounds (dry weight) per day of high value feed mixes must be fed to each animal for maintenance and to produce a daily average increase in weight of $1\frac{1}{2}$ to $2\frac{3}{4}$ pounds. This average animal voids approximately 6 pounds of dry weight per 24 hour period. Typically the manure is merely removed periodically from the confined areas and stockpiled, pressed into blocks and in some cases a small amount has been used on fields as humus. Animal wastes are thus accumulated in localized areas and become sources of air and water pollution. The amount of animal waste generated in the United States is about 10 times that of human waste and 70% of this animal waste is from cattle.

The treatment of animal waste has always received attention but this attention has increased lately because of environmental considerations. Attempts have been made to recover nutrients from manure, see U.S. Pat. Nos. 4,117,175 and 4,018,650. U.S. Pat. No. 3,546,812 teaches treating similar wastes by the addition of microorganisms. U.S. Pat. No. 4,134,749 is also of interest in this area.

Ruminants possess the unique ability to utilize non-protein nitrogen sources to fulfill a major portion of their dietary protein requirements. These include urea and ammonium salts of organic acids such as ammonium lactate, ammonium acetate and ammonium propionate. It has been proven that ammonium salts are equivalent to soybean meal and superior to urea as a nitrogen supplement when fed to feedlot cattle. See "Fermentative Conversion of Potato Processing Wastes into a Crude Protein Feed Supplement by Lactobacilli", Forney, L. J. et al., Vol. 18, Developments in Industrial Microbiology, proceedings of the 33rd general meeting of the Society for Industrial Microbiology, Aug. 14-20, 1976, Jekyl Island, Ga., Pages 135-143.

Thus, there exists the need to treat animal waste either as a soil extender without any environmental concerns or with modification as a feed for cattle.

SUMMARY OF THE INVENTION

My invention embodies a process wherein animal wastes are treated with a particular bacteria and a carbohydrate. The animal waste may be sterilized or not prior to the bacteria digestion.

The fermentation process of my invention preserves the potential food value of the manure (or the fertilizing capabilities of the manure when applied to the soil), increases the protein content of manure by the production of Lactobacillus cell protein, and greatly reduces or completely eliminates pathogenetic bacteria found in these materials resulting in the safe handling transportation and disposal of these materials.

In one aspect of my invention, the carbohydrate admixed with the bacteria and the manure is a fermentable carbohydrate from food processing waste. The processing wastes include wastes from dairy products such as whey, cannery wastes, meat packing wastes, brewery wastes, fish house packing wastes, etc. all of which are characterized by their high levels of fermentable carbohydrates.

In another aspect of my invention, the lactic acid which is produced as a by-product is then reacted with ammonia to produce ammonium lactate (a synthetic protein for ruminants).

In a still further aspect of the invention, the wastes (manure) from cattle feeding lots are combined with wastes from food processing industries and these combined wastes are innoculated with bacteria to provide a usable product.

My invention is broadly directed to a process for the treatment of manure, either raw or sterilized, from ruminants which treatment renders the manure acceptable either as an animal feed, as a fertilizer, or an environmentally acceptable landfill.

My process includes innoculating manure wastes with a bacteria selected from the genus Lactobacillus and admixing therewith a carbohydrate. The carbohydrate may itself be a waste material high in fermentable carbohydrate content which provides the feed for the bacteria. A pH of 4.5 or less is usually required to eliminate the growth of non-lactobacilli bacteria. In my invention, the pH is lowered to about 4.0 or less resulting in a bactericidal and/or bacteriostatic condition for all bacteria other than lactobacilli. The process is carried out at an ambiant temperature of between about 5° to 53° C., say for example, 24°-40° C., preferably 30°-35° C.

Synthetic protein can be produced for ruminant consumption such as by the use of any processing plant waste in which a carbohydrate is present. The carbohydrate is added to the manure and the resulting combination is innoculated with lactobacilli. The lactic acid produced by the lactobacilli is neutralized with aqueous ammonia to form ammonium lactate, a synthetic protein for ruminants. The final product of this recycling process will contain a mixture of ammonium lactate and harmless lactobacilli which is naturally found in the intestinal tract of cattle as well as in the manure.

In the preferred embodiment of my invention, the specific bacteria *L. plantarum* is used.

*L. plantarum* is capable of fermenting all common sugars (except rhamrose) thus, having the ability to digest any industrial carbohydrate waste such as potato processing waste, agricultural waste, vegetable pickling waste, cheese manufacturing waste (whey), packing house waste, sugar refinery waste (molasses) etc. *L. plantarum* is homofermentative non-gas producing. The only significant metabolic product that *L. plantarum* produces is lactic acid. Lastly, my invention may be used to treat per se, agricultural and industrial waste material having a high BOD, the biological oxygen demand caused by fermentable carbohydrates.

DESCRIPTION OF THE PREFERRED EMBODIMENTS

The invention will be described in reference to the treatment of cattle manure as defined hereinafter with a specific bacteria selected from the genus Lactobacillus and a carbohydrate. More specifically, the bacteria preferred is *L. plantarum* and the carbohydrate preferred is any highly fermentable carbohydrate such as lactose.

MAJOR CONSTITUENTS OF ANIMAL MANURE organic nitrogen: 14–13% protein equivalent
carbohydrate: 30–50% (essentially all cellulose and hemi cellulose)
lignin: 5–12%
inorganic salts: 10–12%
BOD: 0.2–0.5 lbs. per lb. of volatile solids
COD: 1.0–1.5 lbs. per lb. of volatile solids
Pollution Implication of Animal Waste, Loehr, R. C., 1968, "A Forward Orientated Review", page 24–53, Federal Water Pollution Control Administration.

For other published tables which are incorporated by reference in this application relating to manure characteristics generally see: the Handbook of Environmental Control, Vol. IV, Wastewater Treatment and Disposal, CRC Press, Cleveland, Ohio, 1974, pages 637–642, Tables 2.4-150 to 2.4-160.

The above tables generally represent the composition of manure treated in accordance with my invention. Typically, the manure prior to treatment, will have water added to it in order to insure ease of mixing of the bacteria and the carbohydrate and relative homogeneity of the mass. The water may be from the aqueous carbohydrate waste solution. Typically, the solids range of the material during treatment should be 3 to 20% on a dry weight basis, preferably 6 to 16%, say for example 12%.

The reduction in bacteria (other than the bacteria used for the acid fermentation process), will be as described in my parent application. That is, after the acid fermentation, the coliform and total gram negative bacteria measurements will be negative. The addition of the lactobacilli and fermentable carbohydrate, whether or not the manure is sterilized prior to the acid fermentation, is sufficient over a predetermined period of time, say three to five days, to lower the pH sufficiently so that the undesirable bacteria is reduced to a level wherein the treated manure in this one-step process renders that treated manure usable either as a feed for animals with the addition of other nutrients or as a fertilizer or land fill.

The fermentable carbohydrate is added to the manure so as to produce a 2 to 4% solution as in the parent application, or by the addition of fermentable carbohydrate present in industrial waste. The fermentable carbohydrates are required as the energy source for the lactobacilli. With sufficient carbohydrate supply the pH of the manure will reach the range of 4.2 to 3.8. Following this acid digestion the pH will remain at this low level inhibiting the regrowth of unwanted bacteria. The pH of the manure slurry during the acid fermentation process determines the total amount of carbohydrate required to be added to the manure. When the manure stabilizes at a pH of between 3.8 to 4.2 no more carbohydrate need be added.

In the treatment of manure, such as from cattle feeding lot operations, the manure is placed in a tank or the like. Depending upon the nature of the source, the percent solids in the manure will vary. If necessary, water is added (pure or in the presence of fermentable carbohydrates) to bring the mass during fermentation to between 6 to 20% solids. The lactobacilli is added preferably $10^2$ cells/ml or higher *L. plantarum;* and the carbohydrate is added and the pH is monitored. Initially, the carbohydrate is added preferably to form a 2 to 4% fermentable carbohydrate solution. After the initial addition, more carbohydrate is added depending upon the pH. After the mass has stabilized at pH of between about 3.8 to 4.2, it is free of pathogenic and gram negative bacteria and may be used as landfill.

Where *L. plantarum* is used, it may be grown and harvested in the manner as set forth in my parent application. The concentrations of bacteria added to the manure will range between about $10^2$ to $10^3$ cells/ml. Preferably the carbohydrate or the disaccharide lactose and the specific bacteria *L. plantarum* are used. The other species of the genus Lactobacillus alone or in combination are also suitable. The temperature range for growth is typically 5°–53° C. The lactobacilli are acidophillic with an optimal initial pH range of 5.5 to 5.8 and clearly grow at a pH of 5.0 or less. The complex nutritional requirements of lactobacilli for amino acids, peptides, nucleic acid derivatives, vitamins, salts, fatty acids or fatty acid esters appear to be present in typical manure. It has been found that additional fermentable carbohydrates, however, must be added to the manure for the pH to drop below 4.5. Any one of the following bacteria or combinations thereof may be used with my invention: *L. acidophilus, L. bulgaricus, L. casei, L. coryniformis, L. delbruckii, L. helveticus, L. lactis, L. leichmannii, L. plantarum, L. thermophilus, L. xylosus, L. brevis, L. buchneri, L. coprophilus, L. fermentum, L. viridenscens.*

The carbohydrates used in the scope of my invention may be any carbohydrate such as amygdalin, arabinose, cellobiose, esculin, fructose, glactose, glucose, gluconate, lactose, maltose, mannitol, mannose, melezitose, melibiose, raffinose, rhamnose, ribosse, salicin, sorbitol, sucrose, trehalose, and xylose or combinations thereof.

When the carbohydrate is added to the manure containing the bacteria, the pH will drop to below 4.5. Further, there is a drastic reduction of all native bacteria normally found in manure. There is approximately a $10^5$ reduction of coliform, total gram negative bacteria and total bacteria (excluding the innoculant bacteria such as *L. plantarum*). The innoculation of lactobaccilli into manure, whether or not presterilized in the presence of additional carbohydrate results in the production of lactic acid. This lactic acid causes the inhibition of growth and death of the vast majority of bacteria normally found in the manure.

In an alternative embodiment of the invention, the industrial processing wastes are the source for the carbohydrate. For purposes of this invention, the wastes are defined as those wastes having a high BOD content in a range of from 200 to 34,000 mg/l. The BOD in this application is determined by fermentable carbohydrate which provides the food source for the bacteria used.

Illustrative processing plant wastes include food wastes such as brewery, distillery, dairy, cannery, slaughterhouse, potato processing, farm and poultry. These wastes are characterized by their high BOD contents. Those wastes which are included within the scope of this invention and which set forth the various BOD amounts are defined in the Hardbook of Environmental Control, supra pages 442, table 2.1-11, 446 table 2.1-16, 448 table 2.1-19, page 441, table 2.1-20, 452, table 2.1-21, page 552, table 2.4-1 and 2, page 555, tables 2.4-7 and 8, 558, table 2.4-13, 559, table 2.4-14, page 570, table 2.4-31 through 33, page 571, table 2.4-34, page 573, table 2.4-35, page 574, table 2.4-36, tables 2.4-37, 38, 39, page 580, tables 2.4-47, 48, page 600, table 2.4-80 and 81, page 611, tables 2.4-401 and 405, and page 636, table 2.4-149 all of which tables are incorporated in their entireties by reference in this application.

As with the preferred embodiment, the wastes are mixed with the bacteria-innoculated manure and the pH is monitored. If the pH does not arrive at 3.8 to 4.2, then additional carbohydrate is added.

In a further alternative embodiment of the invention, the stabilized mass resulting from the above process (either preferred or alternative) may be further treated to produce ammonium lactate, a feed supplement for animals. After the bacteria population of the manure has been stabilized (pathogenic and gram negative bacteria have been killed by exposure to pH of 3.8 to 4.2) aqueous ammonium is bubbled through the manure forming ammonium lactate. The ammonium may be bubbled through in any conventional manner. During the process, the lactobacilli are digesting fermentable carbohydrates and producing lactic acid. The pH during this step is between 4.5 and 5.5. The pH is maintained in this range by controlling both the amount of ammonia and fermentable carbohydrate being added to the manure.

The amount of aqueous ammonia used depends upon the amount of lactic acid produced, the pH of the manure, the buffering capacity of the manure, the rate of production of lactic acid and the extent to which it is desired to carry the reaction to completion, i.e., the final percentage of ammonium lactate to be produced.

In a final embodiment of the invention, the invention is used to stabilize processing plant wastes as defined above having a BOD in mg/l in an amount of from 600 to 32,000. Basically, as with the preferred embodiment, a bacteria is added to the waste material and the pH monitored.

If the processing waste does not stabilize between 3.8 to 4.2 pH, then additional carbohydrate is added until the desired pH range is achieved. At this point, the mass has been stabilized and may be disposed of as environmentally acceptable landfill.

Therefore, my invention contemplates treating manure such as cattle manure by the addition of a bacteria such as *L. plantarum* and a fermentable carbohydrate whereby, without more, the pH of the treated manure falls to below 4.2. This effectively achieves elimination of the pathogenic and gram negative bacteria. Although a solution of purified carbohydrates may be used, it has been found that processing plant waste, as defined within the scope of my invention, may be used as the carbohydrate source. Clearly, combinations of specific carbohydrates as specified above, either alone or in combination with one or more types of processing plant waste may be used.

Lastly, the industrial waste per se may be treated in order to render them free of BOD content and thus suitable for waste disposal.

Having described my invention, what I now claim is:

1. A method for the treatment of manure which treatment renders the manure environmentally acceptable which includes:
    inoculating the manure with Lactobacillus, the manure per se containing the nutritional requirements for the Lactobacillus; and
    admixing a fermentable carbohydrate in an effective amount with manure, the Lactobacillus inoculated and the carbohydrate admixed in an amount sufficient to lower the pH of the manure to below 4.5 whereby the manure is stabilized and rendered substantially free of coliform and pathogenic bacteria.

2. The method of claim 1 wherein the carbohydrate is lactose.

3. The method of claim 1 wherein the Lactobacillus is *L. plantarum*.

4. The method of claim 1 which includes maintaining the manure at a temperature between about 5°–53° C.

5. The method of claim 1 which includes maintaining the temperature of the manure between 32°–35° C.

6. The method of claim 1 wherein the Lactobacillus is *L. plantarum* and the carbohydrate is lactose.

7. The method of claim 1 wherein the bacteria is selected from the group consisting of *L. acidophilus, L. bulgaricus, L. casei, L. coryniformis, L. delbruckii, L. helveticus, L. lactis, L. leichmannii, L. plantarum, L. thermophilus, L. xylosus, L. brevis, L. buchneri, L. coprophilus, L. fermentum, L. viridescens.*

8. The method of claim 7 wherein the bacteria is *L. casei*.

9. The method of claim 1 wherein the carbohydrate is selected from the group consisting of amygdalin, arabinose, cellobiose, esculin, fructose, glactose, glucose, gluconate, lactose, maltose, mannitol, mannose, melezitose, melibiose, raffinose, rhamnose, ribosse, salicin, sorbitol, sucrose, trehalose, and xylose.

10. The method of claim 9 wherein the carbohydrate is glucose.

11. The method of claim 1 wherein the carbohydrate is in industrial waste and which includes admixing the industrial waste having a BOD content of from 200 to 34,000 mg/L with the BOD based on the fermentable carbohydrate in the waste which is a food for the bacteria inoculated in the manure.

12. The method of claim 1 which includes
    contacting the stabilized manure with ammonia in an amount sufficient to convert the lactic acid to ammonium lactate.

13. The method of claim 12 which includes maintaining the pH of the manure between 4.8 to 5.5 while contacted with ammonia.

14. The method of claim 1 wherein the bacteria is *L. casei* and the carbohydrate is glucose.

15. The method of claim 1 wherein the bacteria is *L. plantarum* and the carbohydrate is dextrose.

16. The method of claim 1 wherein the bacteria is *L. casei* and the carbohydrate is dextrose.

17. A method for the treatment of industrial waste which waste has a BOD content of from 200–34,000 mg/l, the BOD based on the fermentable carbohydrate in the waste and which carbohydrate is a food for a bacteria which consists of:
    inoculating the waste with Lactobacillus; and
    supporting the growth of the bacteria until the pH of the waste is between 3.8 to 4.2.

* * * * *